United States Patent
Keene et al.

(10) Patent No.: US 7,308,908 B2
(45) Date of Patent: Dec. 18, 2007

(54) DEVICE AND METHOD FOR CONTROLLING THE FLOW OF FLUID IN A CONDUIT

(75) Inventors: Russell Keene, Sudbury, MA (US); Mark Moeller, Kingston, MA (US); Theodore D. Ciolkosz, Milton, MA (US)

(73) Assignee: Waters Investments Limited, New Castle, DE (US)

( * ) Notice: Subject to any disclaimer, the term of this patent is extended or adjusted under 35 U.S.C. 154(b) by 0 days.

(21) Appl. No.: 11/429,562

(22) Filed: May 5, 2006

(65) Prior Publication Data

US 2006/0260695 A1 Nov. 23, 2006

Related U.S. Application Data

(63) Continuation of application No. PCT/US2004/037640, filed on Nov. 10, 2004.

(60) Provisional application No. 60/523,165, filed on Nov. 10, 2003.

(51) Int. Cl.
*F16K 37/00* (2006.01)
*F16K 11/074* (2006.01)

(52) U.S. Cl. ............. 137/554; 137/625.11; 137/625.46

(58) Field of Classification Search ............... 137/554, 137/625.46, 625.11
See application file for complete search history.

(56) References Cited

U.S. PATENT DOCUMENTS

| | | | |
|---|---|---|---|
| 3,384,118 A | 5/1968 | Heintz et al. | |
| 4,501,297 A | 2/1985 | Baker | |
| 4,846,098 A | 7/1989 | Kobayashi et al. | |
| 6,012,487 A * | 1/2000 | Hauck .................. | 137/625.11 |
| 6,267,143 B1 | 7/2001 | Schick | |
| 6,352,105 B1 | 3/2002 | Serratto | |
| 2005/0199304 A1 | 9/2005 | Poppe et al. | |

* cited by examiner

*Primary Examiner*—John Rivell
(74) *Attorney, Agent, or Firm*—Anthony J. Janiuk (57) ABSTRACT

The present invention provides devices and methods for controlling the flow of fluids in very high pressure situations. The devices feature valve shafts having bearings and pins to hold stator surfaces and rotor surfaces in proper alignment.

39 Claims, 5 Drawing Sheets

DEVICE AND METHOD FOR CONTROLLING THE FLOW OF FLUID IN A CONDUIT

RELATED APPLICATIONS

This application claims benefit of and is a continuation of International Application No. PCT/US2004/037640, filed Nov. 10, 2004 and designating the United States, which claims benefit of a priority to U.S. Provisional Application Ser. No. 60/523,165, filed Nov. 10, 2003. The contents of these applications are expressly incorporated herein by reference in its entirety.

FIELD OF THE INVENTION

The invention relates a to devices and methods for controlling the flow of fluid in a conduit. And, in particular, embodiments of the present invention relate to valves for high pressure applications such as ultra high pressure chromatography.

BACKGROUND OF THE INVENTION

High pressure valves have been used in analytical processes and chromatographic processes in particular. There has been interest in applying higher pressures to obtain faster separations and increase through put. However, at ultra high pressures valves and other components become less reliable.

As used herein, the term "chromatographic processes" refers to processes that separate one compound from another compound as a result of difference in the affinity of the compounds to a stationary phase as the compounds travel in or around such phase.

The term high pressure chromatography refers to chromatographic processes which use pressures up to and including four thousand pounds per square inch. Ultra high pressure chromatography refers to chromatography processes which use pressures of greater than four thousand pounds per square inch.

As pumps and detectors used in analytical processes are operated at higher pressures, components of such equipment exhibit higher rates of failure. The loads on seals, bearing elements, springs and motors is greater. The torque required to turn shafts and axles is greater. As loads increase, alignment and positioning of flow control and sealing features becomes more critical to valve performance and useful lifetime.

It is desirable to have valves that can operate precisely and reliably at very high pressure for chromatography. It is desirable to have a valve that can be serviced to replace parts and components which experience wear and deterioration and retain other elements which remain fully functional.

SUMMARY OF THE INVENTION

Embodiments of the present invention are directed to a device and methods for controlling the flow of fluid in a conduit and methods of making and servicing such a device. The device and methods have particular application in the field of chromatography. However, those skilled in the art of fluidics will recognize the wide application of the devices and methods of the present invention.

One embodiment of the present invention is directed to a device, such as a valve, for controlling the flow of fluid in a conduit. The device comprises a cartridge housing, a valve shaft, valve shaft bearings, a rotor, a stator and pressure means for pressing the rotor against the stator.

The cartridge housing has an interior wall, an exterior wall and an end wall. The interior wall defines a substantially cylindrical chamber. The chamber has a first end, a second end, a chamber axis and at least one diameter. The end wall is at one of the ends and has a bearing opening.

The valve shaft is within the chamber. The valve shaft is capable of rotation and has a valve shaft axis of rotation aligned with the chamber axis. The valve shaft bearings are held in the bearing opening and receive the valve shaft for rotation.

The rotor is coupled to the valve shaft for rotation, positioned at the end of the chamber opposite the end wall. The rotor has a rotor bearing surface having one or more fluid channels.

The stator has at least one stator exterior surface and at least one stator interior surface. The stator interior surface has a stator bearing surface for receiving the rotor bearing surface. The rotor bearing surface and the stator bearing surface cooperate to allow the rotor bearing surface to rotate in relation to the stator bearing surface. The stator is received and fixed about the end of the chamber opposite the end wall. The stator has at least two stator fluid openings. Each of the stator fluid openings extends from the stator exterior to the rotor bearing surface. In alignment with said one or more channels of the rotor, the opening define an open position upon the rotor assuming a first position. And, in alignment with a rotor bearing surface without one or more channels, upon the rotor assuming a second position, the opening have a closed position. Thus, the rotor and the stator have a first position, defining an open position, in which fluids are received in one of the stator fluid openings and flow through the channel and out a second stator fluid opening. And, the stator and the rotor have a closed position in which fluids are prevented from flowing from one stator fluid opening to the other stator fluid opening by means of the rotor bearing surface.

The device has pressure means for pressing said rotor bearing surface against said housing bearing surface such that rotation of the valve shaft and rotor allows fluid flow in one valve shaft position and does not allow fluid flow in a second valve shaft position. The pressure means engage said end wall and said valve shaft. Preferably, the pressure means comprises sealing and pressure springs.

Preferably, the device has stator retaining means securing said stator to the cartridge housing. And, preferably the stator retaining means releasably secures the stator to the cartridge housing to allow the rotor pressure means and shaft to be slidably received in the cartridge housing chamber, and the rotor stacked on the shaft. The stator retaining means preferable is selected from clamps screw fittings and the like. One preferred stator retaining means comprises one or more screws which cooperate with one or more screw openings in the stator and one or more threaded openings in cartridge housing.

Preferably, the device further comprising a rotor pin and wherein the rotor has a rotor pin opening, the stator has a stator pin opening and the shaft has a shaft pin opening. The rotor pin extends through the rotor opening and into the shaft pin opening and the stator pin opening to align the channels of the rotor with said stator fluid openings.

Preferably, the rotor and shaft are keyed. For example, the keying may comprise a shaft having an end hub and the end hub has means for keying the rotor such that said rotor rotates with said rotor shaft. The keying comprises at least one key opening having a position in at least one of the group selected from the rotor and the end hub. The key opening cooperates with and receives a key pin associated with the rotor and end hub that does not have the key opening or extends through key openings in the rotor and end hub.

Preferably, at least one of the group selected from said rotor and said shaft has stop means for preventing angular rotation of the rotor with respect to the housing. This provides means for placing the rotor at the first and/or second positions. One stop means comprises a stop element projecting from the cylindrical wall of the cartridge housing. At least one of the rotor and the shaft has stop abutment surfaces that abut against the stop element to prevent rotation. Preferably, The key pin has a stop abutment surface and the cartridge housing has a stop element projecting from the cylindrical wall. And, preferably, the abutment surface is an alignment pin extending through the cartridge housing into the chamber.

Preferably, at least one of the group selected from the rotor and shaft have position sensing means. The position sensing means produces a signal when the rotor is in the first position or second position. And, even more preferably, the position sensing means produces a first signal when the rotor is in the first position and a second signal when said rotor is in the second position. The position sensing means is for communication with control means. Individuals skilled in the art will recognize control means as computer processing units, CPUs, with appropriate memory and software. The control means receives the signal to determine the position of the rotor.

A preferred position sensing means comprises an optical sensor and light emitter associated with the housing and at least one of the group selected from the shaft and rotor. For example, the shaft and rotor have markings detectable by the optical sensor when illuminated by the light emitter in the nature of bar code readers. A preferred light emitter and optical sensor are affixed to the exterior of the cartridge housing and the cartridge housing has at least one window means in communication with the light emitter and optical sensor to allow light to enter and leave the chamber after illuminating the rotor or shaft.

Preferably, the pressure means comprises at least one spring and sealing means. Preferably, the spring is a floating spring substantially encircling the shaft. As used herein "floating" means that the spring is not secured to the shaft or housing and does not influence rotation. One preferred spring is a belleville assembly. A belleville assembly comprises stacked spring washers having a conical shape which exerts a inward and outward sealing force on the cylindrical wall and shaft when compressed. Preferably, the assembly comprises a thrust bearing allowing rotation without twisting the rotor from the stator.

Preferably, the shaft has a spring hub, for receiving the spring or belleville assembly.

Preferably, the pressure means is adjustable. One embodiment of the present invention features adjustment means comprising an adjustment load spider. The adjustment load spider has legs which cooperate with spider openings in the end wall of the housing. The legs and the openings have cooperating threads. Or, and the alternative the adjustment means comprises an adjustment load spider and the end wall of the housing has a load nut opening. The housing has means for receiving a load nut in communication with the spider to adjust the compression of the spring. For example, the housing has a load nut recess, and the load nut recess has threads for receiving said load nut. The load nut is tightened or loosened to adjust the compression of the springs held in the chamber via the spider's legs through spider openings in the end wall of the housing. The pressure means exerts a pressure on the rotor and stator to maintain a substantially closed system in pressure ranging from 4,000 psi and up. Pressures of up to 40,000 psi may be attained with some embodiments of the present device.

Preferably, the shaft has a toothed coupling for receiving cooperating toothed coupling on a power shaft. And, preferably the power shaft is associated with a transmission for receiving power from a motor. One embodiment of the present invention features a second housing having a first section and a second section. The first section holds the first housing. The second section comprises at least one interior wall, one exterior wall and one end wall. The interior wall defines a cylindrical chamber, and the end wall terminates the chamber. The end wall has an opening for receiving the power shaft. The chamber contains one or more gears constructed and arranged to transfer rotational force from a motor to the power shaft in the manner of a transmission.

Preferably, the device further comprises a motor coupled to the transmission to rotate the power shaft.

Preferably, the shaft sensing means comprises a encoder disk and an encoder. The encoder is affixed to the interior wall of the second housing and the encoder disk is received on the power shaft. The encoder disk has positioning indicia which correlate to the position of the power shaft. Preferably, the encoder disk has an indent which is sized to cooperate with the encoder chip, when such encoder chip is fitted to the interior wall, to allow such encoded disk to be placed in position axially.

Preferably, the device second housing contains power shaft sensing means. The power shaft sensing means producing one or more signals in response to the rotational position of the power shaft.

Preferably, the device has memory means recording the operation of the valve. The memory device is capable of communication with a computer to monitor the number of operations performed to give notice when routine maintenance would be in order.

A further embodiment of the present invention comprises a method of making a device for controlling the flow of fluids in a conduit. The method comprises the steps of providing a cartridge housing having an interior wall, an exterior wall and an end wall. The interior wall defines a substantially cylindrical chamber. The chamber has a first end, a second end, a chamber axis and at least one diameter. The end wall is at one of the ends and has a bearing opening. The method further comprises the step of fitting valve shaft bearings in the bearing opening. Next, pressure means is fitted about the valve shaft. And, the valve shaft placed for rotation within the chamber. The valve shaft is capable of rotation and has a valve shaft axis of rotation aligned with the chamber axis. The pressure means is for pressing a rotor bearing surface against a stator bearing surface such that rotation of the valve shaft and rotor allows fluid flow in one valve shaft position and does not allow fluid flow in a second valve shaft position. The pressure means engage said end wall and said valve shaft. Preferably, the pressure means comprises sealing and pressure springs. Next, the rotor is coupled to the valve shaft for rotation, positioned at the end of the chamber opposite the end wall. The rotor has a rotor bearing surface having one or more channels. A stator is fitted to the cartridge housing. The stator has at least one stator exterior surface and at least one stator interior surface. The stator interior surface has a stator bearing surface for receiving the rotor bearing surface. The rotor bearing surface and the stator bearing surface cooperate to allow the rotor bearing surface to rotate in relation to the stator bearing surface. The stator is received and fixed about the end of the chamber opposite the end wall. The stator has at least two stator fluid openings. Each of the stator fluid openings extends from the stator exterior to the rotor bearing surface. In alignment with said one or more channels of the rotor, the opening define an open position upon the rotor assuming a first position. And, in alignment with a rotor bearing surface without one or more channels, upon the rotor assuming a second position, the opening have a closed position. Thus, the rotor and the stator have a first position, defining an open position, in which fluids are received in one of the stator fluid openings and flow through the channel and out a second stator fluid opening. And, the stator and the rotor have a closed position in which fluids are prevented from flowing from one stator fluid opening to the other stator fluid opening by means of the rotor bearing surface.

Preferably, the method uses stator retaining means securing said stator to the cartridge housing. And, preferably the stator retaining means releasably secures the stator to the cartridge housing to allow the rotor pressure means and shaft to be slidably received in the cartridge housing chamber, and the rotor stacked on the shaft. Thus the device can be dismantled for servicing.

Preferably, the method further comprises fitting a rotor pin. In this embodiment the rotor has a rotor pin opening, the stator has a stator pin opening and the shaft has a shaft pin opening. The rotor pin extends through the rotor pin opening and into the shaft pin opening and the stator pin opening to align the channels of the rotor with said stator fluid openings.

Preferably, the method further comprises the step of affixing the rotor and valve shaft by fitting a key. For example, the keying may comprise a shaft having an end hub and the end hub has means for keying the rotor such that said rotor rotates with said rotor. Preferably, the keying comprises at least one key opening having a position in at least one of the group selected from the rotor and the end hub. The key opening cooperates with and receives a key pin associated with the rotor and end hub that does not have the key opening or extends through key openings in the rotor and end hub.

Preferably, the method comprises the step of fitting stop means. At least one of the group selected from said rotor and said shaft has stop means for preventing angular rotation of the rotor with respect to the housing. This provides means for placing the rotor at the first and/or second positions. One stop means comprises a stop element projecting from the cylindrical wall of the cartridge housing. At least one of the rotor and the shaft has stop abutment surfaces that abut against the stop element to prevent rotation. Preferably, The key pin has a stop abutment surface and the cartridge housing has a stop element projecting from the cylindrical wall. And, preferably, the abutment surface is an abutment pin extending through the cartridge housing into the chamber.

Preferably, the method further comprises one or more of the following fitting a position sensing means, control means, transmission means and motor means.

A further embodiment of the present invention is directed to a method of controlling the flow of fluid in a conduit. The method comprises the steps of providing in the conduit a device having a cartridge housing, a valve shaft, valve shaft bearings, a rotor, a stator and pressure means for pressing the stator against the rotor as described above.

These and other features and advantages of the present invention will be apparent to individuals skilled in the art upon studying the drawings and detailed description that follow.

DETAILED DESCRIPTION OF THE INVENTION

Embodiments of the present invention will be described in detail as a device and methods for controlling the flow of fluid in a conduit and methods of making and servicing such a device. The device and methods have particular application in the field of chromatography. However, those skilled in the art of fluidics will recognize the wide application of the devices and methods of the present invention in areas other than chromatography and analytical processes. Indeed, embodiments of the present invention have application wherever valves are used.

Figure 1:
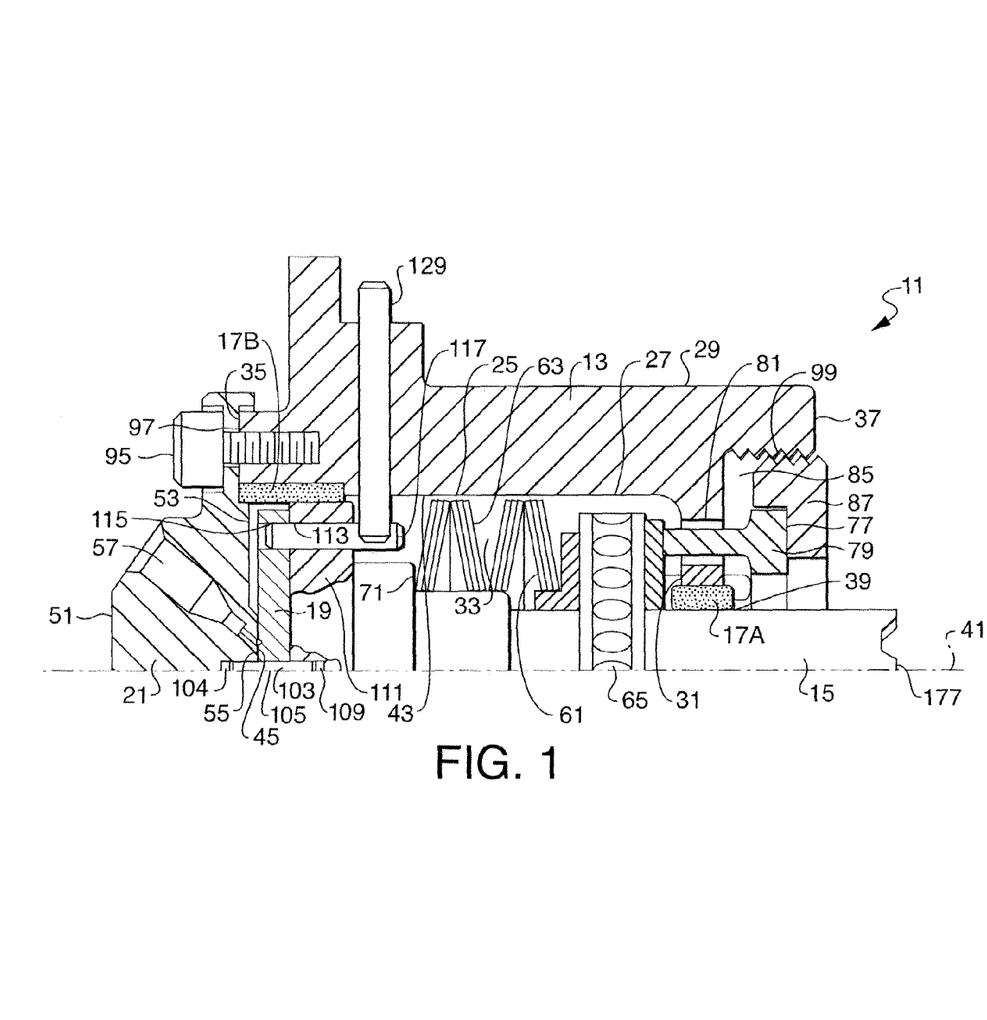
FIG. 1 depicts in cutaway quarter section a device embodying features of the present invention.

Embodiment of the present invention, directed to a device, such as a valve, for controlling the flow of fluid in a conduit will be described in detail with respect to the Figures. Turning now to FIG. 1, a device 11, embodying features of the present invention is depicted. The device 11 comprises a cartridge housing 13, a valve shaft 15, valve shaft bearings 17 A & B, a rotor 19, a stator 21 and pressure means 25 for pressing the rotor 19 against the stator 21.

Cartridge housing 13 has an interior wall 27, an exterior wall 29 and an end wall 31. The interior wall 27 defines a substantially cylindrical chamber 33. The chamber 33 has a first end 35, a second end 37, a chamber axis 41 and at least one diameter 43. The end wall 31 is at one of the ends 37 and has a bearing opening 39.

Valve shaft 15 is held within the chamber 33. Valve shaft 15 is capable of rotation and has a valve shaft axis of rotation aligned with the chamber axis 41. Valve shaft bearing 17A is held in the bearing opening 39 and receives valve shaft 15 for rotation. Valve shaft bearing 7B is held in end 35 of chamber 33 opposite the end wall 27.

Figure 2:
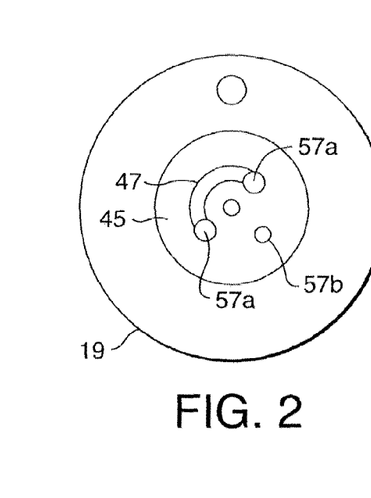
FIG. 2 depicts a rotor embodying features of the present invention.

Valve shaft 15 is held in valves shaft bearing 17 A & B. Rotor 19 is affixed to valve shaft 15, proximal to stator 21, for rotation, positioned at the end 35 of the chamber 33 opposite the end wall 27. Turning briefly to FIG. 2, rotor 19 has a rotor bearing surface 45 having one or more channels 47 of which only one is depicted.

The stator 21 has at least one stator exterior surface 51 and at least one stator interior surface 53. The stator interior surface 53 has a stator bearing surface 55 for receiving the rotor bearing surface 45. The rotor bearing surface 45 and the stator bearing surface 55 cooperate to allow the rotor bearing surface 45 to rotate in relation to the stator bearing surface 55.

Stator 21 is received and fixed about the end 35 of the chamber 33 opposite the end wall 31. Stator 21 has at least two stator fluid openings 57 of which only one is shown in FIG. 1. Each of the stator fluid openings 57 extends from the stator exterior 51 to the rotor bearing surface 55. In alignment with said one or more channels 47 of the rotor 19, the openings 57 define an open position upon the rotor 19 assuming a first position. This first position is depicted in FIG. 2 where circles 57a represent opening 57 at the end of channel 47.

And, in alignment with a rotor bearing surface 45, in which the opening 57 are not in communication with one or more channels, as depicted in FIG. 2 by the circles 57b, upon the rotor assuming a second position, the opening 57 have a closed position. Thus, rotor 19 and stator 21 have a first position, defining an open position, in which fluids are received in one of the stator fluid openings 57 and flow through channel 47 and out a second stator fluid opening 57. And, stator 21 and the rotor 19 have a closed position in which fluids are prevented from flowing from one stator fluid opening 57 to the other stator fluid opening 57 by means of the rotor bearing surface 45.

Device 11 has pressure means 25 for pressing said rotor bearing surface 45 against stator bearing surface 55 such that rotation of the valve shaft 15 and rotor 19 allows fluid flow in one valve shaft position and does not allow fluid flow in a second valve shaft position. The pressure means 25 engages the end wall 31 and valve shaft 15. Preferably, pressure means 25 comprises bearings and springs. Preferably, the springs are floating, substantially encircling the shaft. As used herein "floating" means that the spring is not secured to the shaft or housing and does not influence rotation. One preferred spring and seal is a belleville assembly 61. A belleville assembly 61 comprises stacked spring washers 63. Each spring washer 63 has a conical shape which exerts a inward force on the valve shaft 15 and an outward sealing force on the loading nut 77 when compressed. The amount of compression that the belleville assembly can resist and reassert on the rotor 19 is controlled by the number and placement of the washers 63 in chamber 33. Preferably, the belleville assembly 63 comprises a thrust bearing 65 allowing rotation of valve shaft 15 without undue friction.

Valve shaft 15 has a shoulder 71, for receiving the spring washers 63 of belleville assembly 61.

Preferably, the pressure means 21 is adjustable. One embodiment of the present invention features adjustment means 77 comprising an adjustment load nut 87 and load spider 79. The adjustment load nut 87 has threads which cooperate with threads in cartridge housing 13. The spider washer 79 has legs which co-operate with slots 81 in the end wall 31 of the cartridge housing 13. In the alternative, as depicted, the adjustment means 77 comprises an adjustment load spider 79 and the end wall 31 of the housing 13 has a load nut opening 85. The cartridge housing 13 has a threaded load nut recess 85 for receiving a load nut 87 in communication with the adjustment load spider 79 to adjust the compression of the belleville assembly 61. The load nut 87 is tightened or loosened to adjust the compression of the springs 63 held in the chamber. The pressure means exerts a pressure on the rotor 19 and stator 21 to maintain a substantially closed system in pressure ranging from 4,000 psi and up. Pressures of up to 40,000 psi may be attained with some embodiments of the present device 11.

Stator retaining means 95 releasably secures the stator 21 to the cartridge housing 13. The stator retaining means 95 is selected from clamps [not shown], screw fittings and the like. As depicted stator retaining means 95 comprises one or more screws which cooperate with one or more screw openings 97 in stator 21 and one or more threaded openings 99 in cartridge housing 13. Stator retaining means 95 releasably secures the stator 21 to the cartridge housing 13 to allow pressure means 25 and valve shaft 15 to be slidably received in the cartridge housing chamber 33, and the rotor 19 stacked on the valve shaft 15.

A rotor pin 103 is received in stator pin opening 104, rotor pin opening 105, and shaft pin opening 109. The rotor pin 103 extends from stator pin opening 104 through the rotor opening 105 and into the shaft pin opening 109 to align the channels 47 of the rotor 19 with said stator fluid openings 57.

Rotor 19 and valve shaft 15 are keyed for unison rotation. As depicted in FIG. 1, valve shaft 15 has an integral end hub 111. End hub 111 has at least one hub key opening 113 and rotor 19 has at least one rotor key opening 115. The hub key opening 113 and rotor key opening cooperate and receives a key pin 117. In the alternative, the rotor 19 and end hub 111 have other key means such as interfitting knobs and indents, or teeth.

As depicted in FIG. 1, rotor 19 and valve shaft 15 have stop means 129 for preventing angular rotation with respect to the cartridge housing 13. Stop means 129 facilitates placing the rotor 19 at the first and/or second positions. Stop means 129 comprises a stop pin projecting from the cylindrical wall 33 of the cartridge housing 13. Rotor 19 and the valve shaft 15 have stop abutment surfaces that abut against the stop pin 129 to prevent rotation. Key pin 117 has a stop abutment surface constructed and arranged to cooperate with stop pin 129. Preferably, stop pin 129 extends through the cartridge housing 13 into the exterior to provide angular position of the cartridge assembly 11 in the housing.

Figure 3:
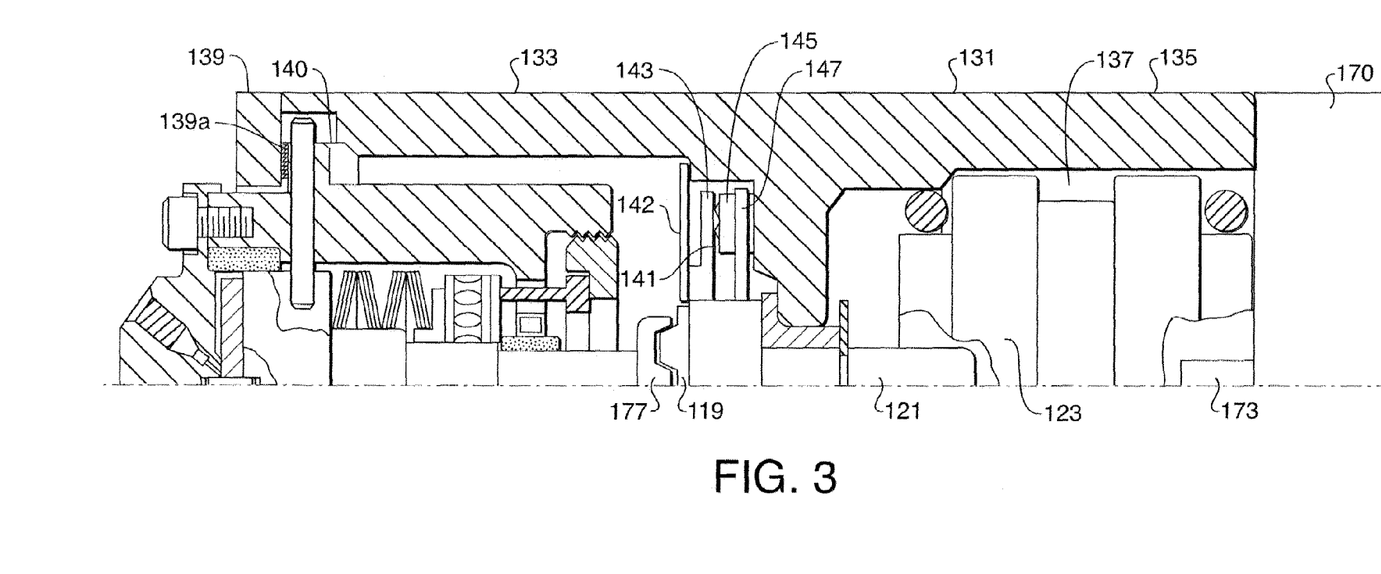
FIG. 3 depicts in cutaway quarter section a device embodying features of the present invention.

Valve shaft 15 has a toothed coupling 177 for receiving cooperating toothed coupling 119 on a power shaft 121, as best seen in FIG. 3. Power shaft 121 is associated with a transmission 123 for receiving power from a motor 170. As depicted device 11 further comprises a second housing 131 having a first section 133 and a second section 135. The first section 133 holds the cartridge housing 13. The rotor 19 position is oriented in the housing 131. The centering ring 139 provides center location of the cartridge assembly 11 in the second housing 131, as best seen in FIG. 3. The second section 135 defines a cylindrical chamber 137 for containing one or more gears 123 constructed and arranged to transfer rotational force from a motor 171 to the power shaft 121 in the manner of a transmission.

Stop pin 129 cooperates with a centering groove 146 in the second housing 131 to facilitate the mounting of the cartridge housing 13 in the second housing 131. A centering ring 139 and ring spring 139a centers and aligns the cartridge housing 13 in the second housing 131. Centering ring 139 is affixed to second housing 131 by cooperating threads [not shown] or screws and threaded openings [not shown].

Figure 6:
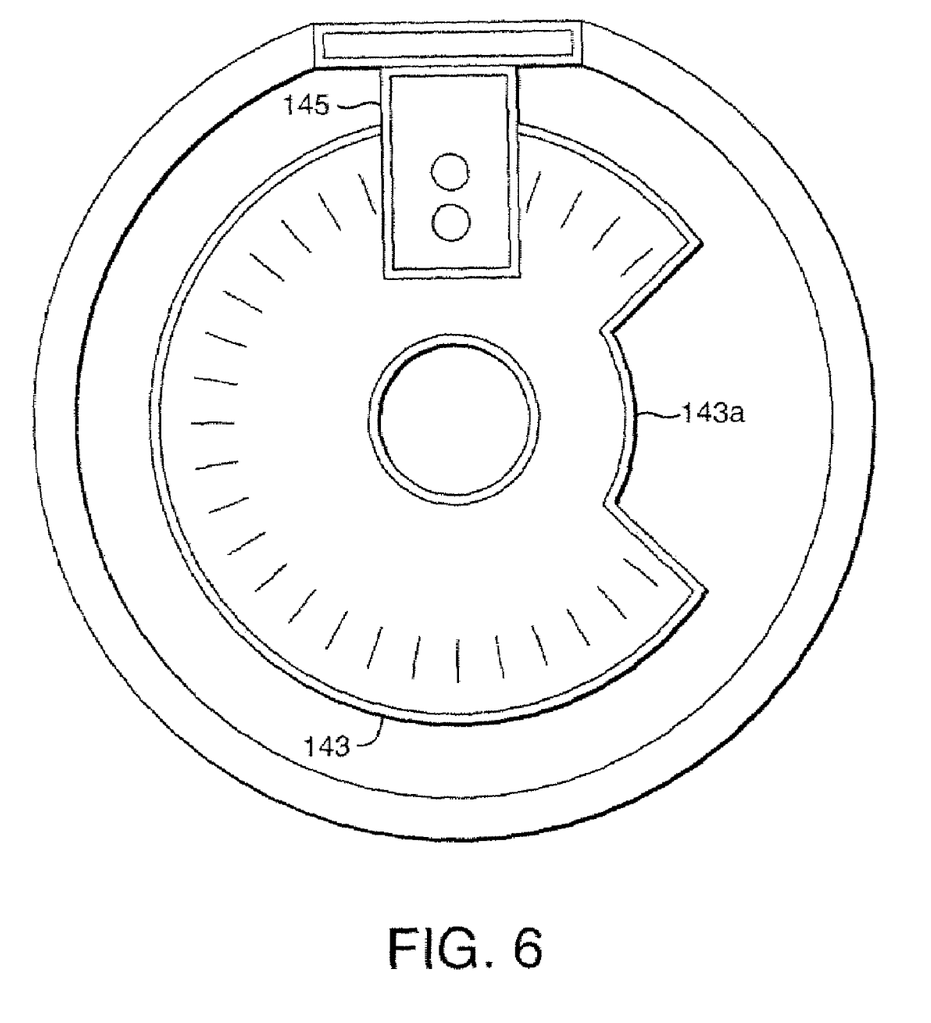

The second housing contains power shaft, rotor or valve shaft sensing means. FIG. 3 depicts power shaft sensing means 141 for producing one or more signals in response to the rotational position of the power shaft 121. Power shaft sensing means 141 comprises an encoder disc 143 and an encoder chip 145. Encoder chip 145 is mounted on an encoder chip support 147. The power shaft sensing means 141 is shielded from the rest of the cartridge housing 13 by an encoder cover 142. Turning now to FIG. 6, the encoder disc 143 has an indent 143a sized to allow axial insertion of the encoder disc 143 on the power shaft 121 and rotated into position under the encoder chip 145.

Figure 4:
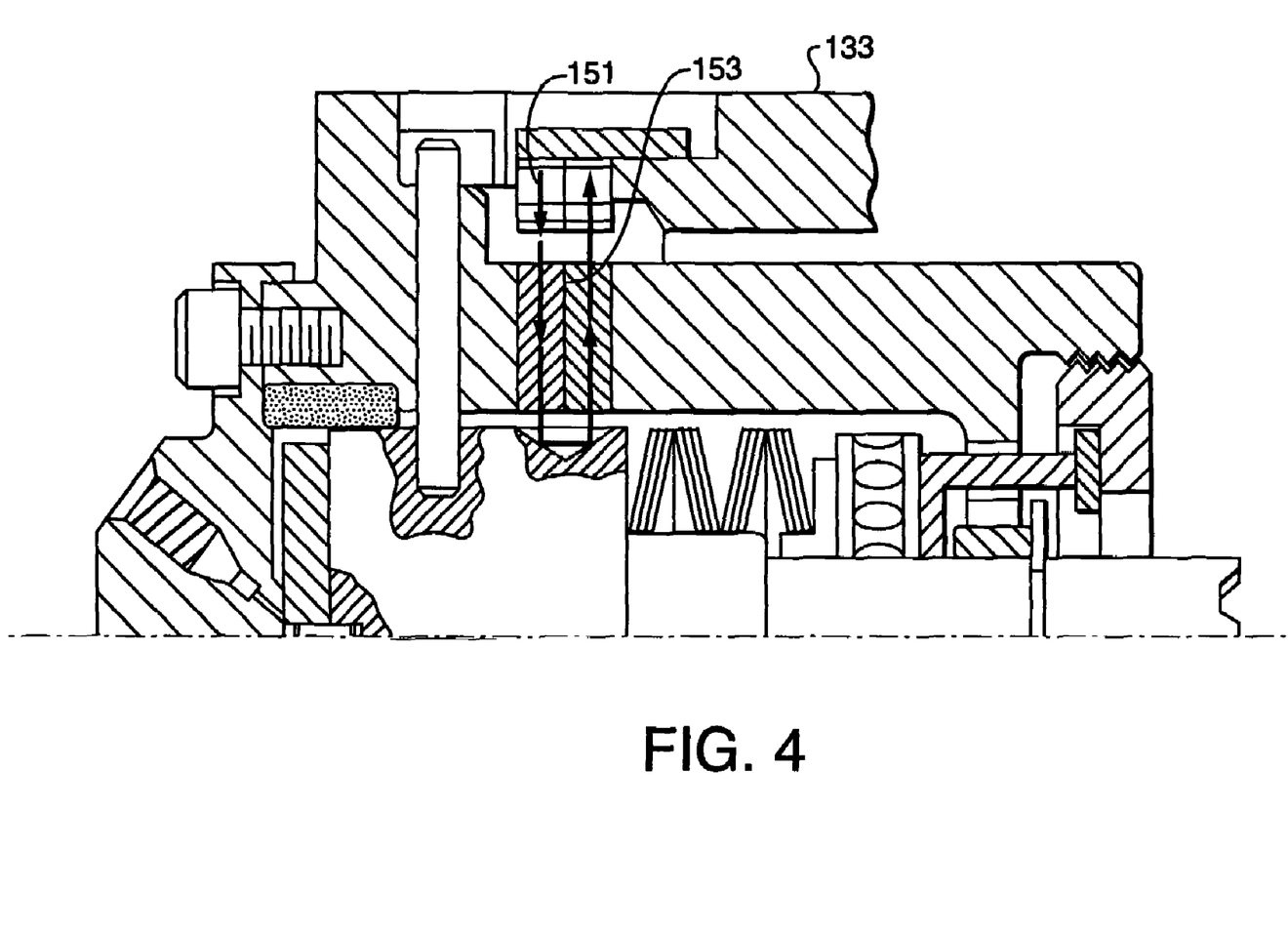
FIG. 4 depicts in cutaway quarter section a device embodying features of the present invention.

Alternatively, the rotor 19 and valve shaft 15 have means for determining the position of the rotor 19. Turning now to FIG. 4, device 11 is illustrated having an optical sensor and light emitter 151 associated with second housing 133. Optical sensor and light emitter 151 cooperates with a fiber optic pair 153 extending through an opening in the cartridge housing 13 to illuminate and read marking [not shown] on the valve shaft 15. Alternatively, the optical sensor and emitter 151 and fiber optic pair 153 cooperate with the markings [not shown] on rotor 19. Markings, in the form of bar code type markings known in the art, are detectable by the optical sensor when illuminated by the light emitter.

The optical sensor and light emitter 151 produces a signal when the rotor 19 is in the first position and a second signal when the rotor is in the second position. The position sensing means 141 and optical sensor and light emitter 151 are in communication with control means [not shown]. Individuals skilled in the art will recognize control means as computer processing units, CPUs, with appropriate memory and software. The control means receives the signal to determine the position of the rotor.

Figure 5:
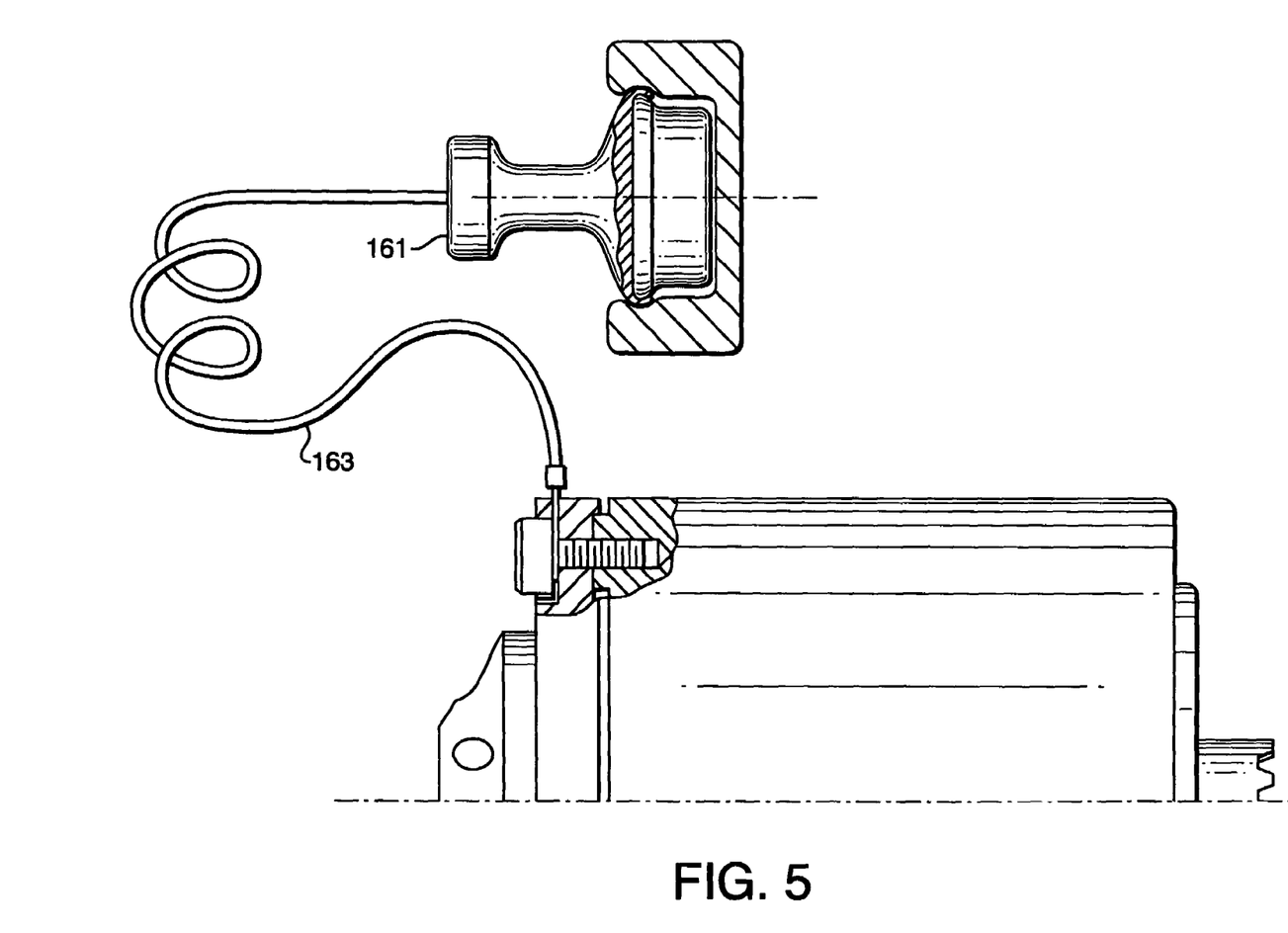
FIG. 5 depicts in partial cutaway quarter section a device embodying features of the present invention; and, FIG. 6 depicts in cutaway a device embodying features of the present invention.

Turning now to FIG. 5, the device 11 has memory disc 161 attached by means of a cable 163. The memory disc 161 is capable of communication with a computer to update and monitor the number of operations performed to give notice when routine maintenance would be in order. Memory disc 161 is sold by several vendors such as Dallas Semi conductor.

A further embodiment of the present invention comprises a method of making a device 11 for controlling the flow of fluids in a conduit. The method comprises the steps of providing a cartridge housing 13 having an interior wall 27, an exterior wall 29 and an end wall 31. The interior wall 27 defines a substantially cylindrical chamber 33. The chamber 33 has a first end 35, a second end 37, a chamber axis 41 and at least one diameter 43. The end wall 29 is at one of the ends 37 and has a bearing opening 39. The method further comprises the step of fitting valve shaft bearings 17 in the bearing opening 39. Next, pressure means 25 is fitted about the valve shaft and the valve shaft 15 is placed within the chamber 33. The valve shaft 15 is capable of rotation and has a valve shaft axis of rotation aligned with the chamber axis 41. The pressure means 25 engages end wall 31, load nut 87 and the valve shaft 15. Next, the rotor 19 is coupled to the valve shaft 15 for rotation, positioned at the end 35 of the chamber 33 opposite the end wall 31. The rotor 19 has a rotor bearing surface 45 having one or more channels 47. A stator 21 is fitted to the cartridge housing 13. The stator 21 has a stator bearing surface 55 for receiving the rotor bearing surface 45. The rotor bearing surface 45 and the stator bearing surface 55 cooperate to allow the rotor bearing surface 45 to rotate in relation to the stator bearing surface 55. The stator 21 is received and fixed about the end of the chamber 33 opposite the end wall 31. The cartridge housing 13 is fitted to a second housing 133 and a motor 171.

Preferably, the method uses stator retaining means 95 securing said stator 21 to the cartridge housing 13. And, preferably the stator retaining means 95 releasably secures the stator 21 to the cartridge housing 13 to allow the pressure means 25 and valve shaft 15 to be slidably received and/or removed from chamber 33. Thus the device can be dismantled for servicing.

Preferably, the method further comprises fitting a rotor pin 103 and abutment pin 115. And, preferably, the spider 79 is adjusted to create an appropriate pressure in the pressure means 25. And, finally, the second housing 133 having position sensing means, transmission gears 123 and motor 170 is secured to the cartridge housing 13.

A further embodiment of the present invention is directed to a method of controlling the flow of fluid in a conduit. The method is described in relationship to the operation of the device 11. The method comprises the steps of providing in the conduit a device 11 having a cartridge housing 13, a valve shaft 15, valve shaft bearings 17, a rotor 19, a stator 21 and pressure means 25 for pressing the stator against the rotor as described above.

The stator 21 has at least two stator fluid openings 57. Each of the stator fluid openings 57 extends from the stator exterior 51 to the rotor bearing surface 45. In alignment with said one or more channels 47 of the rotor 19, the openings 57 define an open position upon the rotor 19 assuming a first position. And, in alignment with a rotor bearing surface 45 without one or more channels 47, upon the rotor assuming a second position, the openings 57 have a closed position. Thus, the rotor 19 and the stator 21 have a first position, defining an open position, in which fluids are received in one of the stator fluid openings 57 and flow through the channel 47 and out a second stator fluid opening 57. And, the stator 21 and the rotor 19 have a closed position in which fluids are prevented from flowing from one stator fluid opening 57 to the other stator fluid opening 57 by means of the rotor bearing surface 45.

Thus, the present invention has been described with respect to a preferred embodiment with the understanding that the invention should not be limited to such description but should encompass the subject matter of the following claims.

What is claimed is:

1. A device for controlling the flow of fluid in a conduit, comprising:
   a. a first housing having at least one interior wall and an exterior wall, said at least one interior wall defining a substantially cylindrical chamber, said chamber having a first end, a second end, a chamber axis and at least one diameter, at least one of said first end and second end having an end wall having a bearing opening;
   b. a valve shaft positioned within said chamber, said valve shaft having a valve shaft axis of rotation aligned with said chamber axis, said valve shaft capable of rotation about said valve shaft axis of rotation;
   c. valve shaft bearings held in said bearing opening and receiving said shaft for rotation;
   d. rotor coupled to said shaft for rotation therewith positioned at one of said first end and second end opposite said end wall, said rotor having a rotor bearing surface having one or more channels;
   e. stator having at least one stator exterior surface and at least one stator interior surface, said stator interior surface having a stator bearing surface said stator bearing surface for receiving a rotor bearing surface and allowing said rotor bearing surface to rotate in relation to said stator bearing surface, said stator removably received about said end of said chamber opposite said bearing opening, said stator having at least two stator fluid openings, each of said stator fluid openings extending from said stator exterior to said rotor bearing surface in alignment with said one or more channels to define an open position upon the rotor assuming a first position and in alignment with a rotor bearing surface without one or more channels upon the rotor assuming a second position to define a closed position, said first position defining an open position in which fluids are received in one of said stator fluid openings and flow through said channel and out a second stator fluid opening and a closed position in which fluids are prevented from flowing from one stator fluid opening to the other stator fluid opening by means of the rotor bearing surface;

f. pressure means for exerting a pressure on said rotor and said stator to press said rotor bearing surface against said stator bearing surface such that rotation of the valve shaft and rotor allows fluid flow in one valve shaft position and does not allow fluid flow in a second valve shaft position said pressure means engaging said end wall and said valve shaft; and, g. adjustment means for adjusting said pressure exerted by said pressure means wherein said adjustment means comprises adjustment load spider and wherein said end wall of said housing has a spider opening which cooperates with said adjustment load spider to allow adjustment of the spring compression.

2. The device of claim 1 further comprising stator retaining means securing said stator to said housing.

3. The device of claim 2 wherein said stator retaining means releasably secures said stator to said housing to allow said rotor pressure means and shaft to be slidably received by said stator openings.

4. The device of claim 3 wherein said stator retaining means is one or more screws and said stator has one or more screw openings cooperating with one or more threaded openings in said housing.

5. The device of claim 1 further comprising a rotor pin and said rotor has a rotor pin opening, said stator has a stator pin opening and said shaft has a shaft pin opening, said rotor pin extending through said rotor opening and into said shaft pin opening and said stator pin opening to align said channels of said rotor with said stator fluid openings.

6. The device of claim 1 wherein said rotor and shaft are keyed.

7. The device of claim 1 wherein said shaft has an end hub for and said end hub has means for keying said rotor such that said rotor rotates with said rotor shaft.

8. The device of claim 7 wherein said means for keying comprises at least one key opening having a position in one of the group selected from the rotor and the end hub, said key opening cooperation with and receiving a key pin associated with the rotor and end hub that does not have the key opening.

9. The device of claim 8 wherein at least one of the group selected from said rotor and said shaft has stop means for preventing angular rotation of the rotor with respect to the housing.

10. The device of claim 9 wherein said stop means comprises a stop element projecting from the cylindrical wall of said housing, and at least one of said rotor and said shaft have stop abutment surfaces which abut against said stop element to prevent rotation.

11. The device of claim 9 wherein said key pin has a stop abutment surface and said housing has a stop element projecting from the cylindrical wall.

12. The device of claim 11 wherein said stop element is an alignment pin extending through the housing into said chamber.

13. The device of claim 1 wherein at least one of said rotor and shaft have position sensing means, said position sensing means producing a signal when said rotor is in said first position and a second signal when said rotor is in the second position.

14. The device of claim 13 further comprising control means in communication with said position sensing means said control means receiving said signal to determine the position of said rotor.

15. The device of claim 13 wherein said position sensing means comprises an optical sensor and light emitter associated with said housing and at least one of said shaft and rotor have markings detectable by said optical sensor when illuminated by said light emitter.

16. The device of claim 15 wherein said light emitter and optical sensor are affixed to the exterior of said housing and said housing has at least one window means in communication with said light emitter and optical sensor.

17. The device of claim 1 wherein said pressure means comprises at least one spring.

18. The device of claim 17 wherein said spring is a floating spring substantially encircling said shaft.

19. The device of claim 17 wherein said spring has two spring ends and wherein said shaft has a spring hub, said spring hub for receiving one of said spring ends.

20. The device of claim 17 wherein said pressure means further comprises at least one thrust bearing assembly, said thrust bearing assembly and spring interposed between said housing and said rotor permitting rotation of the shaft with respect to said housing without binding said spring.

21. The device of claim 1 wherein said housing has means for receiving a load nut in communication with said spider to adjust the compression of said spring.

22. The device of claim 21 wherein said housing has a load nut recess, said load nut recess having threads for receiving said load nut.

23. The device of claim 1 wherein said shaft has toothed coupling for receiving cooperating toothed coupling on a power shaft.

24. The device of claim 23 further comprising a power shaft for coupling with a motor, said power shaft having cooperating toothed coupling received in toothed coupling of said shaft.

25. The device of claim 23 further comprising a transmission for receiving power from a motor.

26. The device of claim 25 further comprising a second housing having a first section and a second section, said first section holding said first housing and said second section comprising at least one interior wall, one exterior wall and one end wall, said interior wall defines a cylindrical chamber, and said end wall terminating said chamber, said end wall having a opening for receiving a power shaft, said chamber for containing one or more gears constructed and arranged to transfer rotational force from a motor to said power shaft.

27. The device of claim 26 further comprising a motor coupled to said transmission to rotate said power shaft.

28. The device of claim 26 wherein said second housing contains power shaft sensing means, said power shaft sensing means producing one or more signals in response to the rotational position of said power shaft.

29. The device of claim 26 further comprising a centering ring for aligning and retaining said first housing to said second housing.

30. The device of claim 1 wherein said first housing has memory means recording the operation of the valve.

31. A method of making a device for controlling the flow of fluids in a conduit comprising the steps of providing and assembling:

a. a first housing having at least one interior wall and an exterior wall, said at least one interior wall defining a substantially cylindrical chamber, said chamber having a first end, a second end, a chamber axis and at least one diameter, at least one of said first end and second end having an end wall having a bearing opening;

b. a valve shaft positioned within said chamber, said valve shaft having a valve shaft axis of rotation aligned with said chamber axis, said valve shaft capable of rotation about said valve shaft axis of rotation;

c. valve shaft bearings held in said bearing opening and receiving said shaft for rotation;

d. rotor coupled to said shaft for rotation therewith positioned at one of said first end and second end opposite said end wall, said rotor having a rotor bearing surface having one or more channels;

e. stator having at least one stator exterior surface and at least one stator interior surface, said stator interior surface having a stator bearing surface said stator bearing surface for receiving a rotor bearing surface and allowing said rotor bearing surface to rotate in relation to said stator bearing surface, said stator removably received about said end of said chamber opposite said bearing opening, said stator having at least two stator fluid openings, each of said stator fluid openings extending from said stator exterior to said rotor bearing surface in alignment with said one or more channels to define an open position upon the rotor assuming a first position and in alignment with a rotor bearing surface without one or more channels upon the rotor assuming a second position to define a closed position, said first position defining an open position in which fluids are received in one of said stator fluid openings and flow through said channel and out a second stator fluid opening and a closed position in which fluids are prevented from flowing from one stator fluid opening to the other stator fluid opening by means of the rotor bearing surface; and, f. pressure means for exerting a pressure on said rotor and said stator to press said rotor bearing surface against said stator bearing surface such that rotation of the valve shaft and rotor allows fluid flow in one valve shaft position and does not allow fluid flow in a second valve shaft position said pressure means engaging said end wall and said valve shaft; and, g. adjustment means for adjusting said pressure exerted by said pressure means wherein said adjustment means comprises adjustment load spider and wherein said end wall of said housing has a spider opening which cooperates with said adjustment load spider to allow adjustment of the spring compression.

32. A method of controlling the flow of fluid in a conduit comprising the step of placing said conduit into fluid communication with a device comprising:

a. a first housing having at least one interior wall and an exterior wall, said at least one interior wall defining a substantially cylindrical chamber, said chamber having a first end, a second end, a chamber axis and at least one diameter, at least one of said first end and second end having an end wall having a bearing opening;

b. a valve shaft positioned within said chamber, said valve shaft having a valve shaft axis of rotation aligned with said chamber axis, said valve shaft capable of rotation about said valve shaft axis of rotation;

c. valve shaft bearings held in said bearing opening and receiving said shaft for rotation;

d. rotor coupled to said shaft for rotation therewith positioned at one of said first end and second end opposite said end wall, said rotor having a rotor bearing surface having one or more channels;

e. stator having at least one stator exterior surface and at least one stator interior surface, said stator interior surface having a stator bearing surface said stator bearing surface for receiving a rotor bearing surface and allowing said rotor bearing surface to rotate in relation to said stator bearing surface, said stator removably received about said end of said chamber opposite said bearing opening, said stator having at least two stator fluid openings, each of said stator fluid openings extending from said stator exterior to said rotor bearing surface in alignment with said one or more channels to define an open position upon the rotor assuming a first position and in alignment with a rotor bearing surface without one or more channels upon the rotor assuming a second position to define a closed position, said first position defining an open position in which fluids are received in one of said stator fluid openings and flow through said channel and out a second stator fluid opening and a closed position in which fluids are prevented from flowing from one stator fluid opening to the other stator fluid opening by means of the rotor bearing surface; and, f. pressure means for exerting a pressure on said rotor and said stator to press said rotor bearing surface against said stator bearing surface such that rotation of the valve shaft and rotor allows fluid flow in one valve shaft position and does not allow fluid flow in a second valve shaft position said pressure means engaging said end wall and said valve shaft; and, g. adjustment means for adjusting said pressure exerted by said pressure means wherein said adjustment means comprises adjustment load spider and wherein said end wall of said housing has a spider opening which cooperates with said adjustment load spider to allow adjustment of the spring compression;

such that the flow of fluid is controlled by the rotor assuming a first or a second position.

33. A device for controlling the flow of fluid in a conduit, comprising:

a. a first housing having at least one interior wall and an exterior wall, said at least one interior wall defining a substantially cylindrical chamber, said chamber having a first end, a second end, a chamber axis and at least one diameter, at least one of said first end and second end having an end wall having a bearing opening;

b. a valve shaft positioned within said chamber, said valve shaft having a valve shaft axis of rotation aligned with said chamber axis, said valve shaft capable of rotation about said valve shaft axis of rotation;

c. valve shaft bearings held in said bearing opening and receiving said shaft for rotation;

d. rotor coupled to said shaft for rotation therewith positioned at one of said first end and second end opposite said end wall, said rotor having a rotor bearing surface having one or more channels;

e. stator having at least one stator exterior surface and at least one stator interior surface, said stator interior surface having a stator bearing surface said stator bearing surface for receiving a rotor bearing surface and allowing said rotor bearing surface to rotate in relation to said stator bearing surface, said stator removably received about said end of said chamber opposite said bearing opening, said stator having at least two stator fluid openings, each of said stator fluid openings extending from said stator exterior to said rotor bearing surface in alignment with said one or more channels to define an open position upon the rotor assuming a first position and in alignment with a rotor bearing surface without one or more channels upon the rotor assuming a second position to define a closed position, said first position defining an open position in which fluids are received in one of said stator fluid openings and flow through said channel and out a second stator fluid opening and a closed position in which fluids are prevented from flowing from one stator fluid opening to the other stator fluid opening by means of the rotor bearing surface; and, f. pressure means for pressing said rotor bearing surface against said stator bearing surface such that rotation of the valve shaft and rotor allows fluid flow in one valve shaft position and does not allow fluid flow in a second valve shaft position said pressure means engaging said end wall and said valve shaft;

g. position sensing means comprising an optical sensor and light emitter affixed to the exterior of said housing, said housing having at least one window means in communication with said light emitter and optical sensor, and at least one of said shaft and rotor have markings detectable by said optical sensor when illuminated by said light emitter, said position sensing means producing a signal when said rotor is in said first position and a second signal when said rotor is in the second position.

34. The device of claim 33 wherein said stop element is an alignment pin extending through the housing into said chamber.

35. A device for controlling the flow of fluid in a conduit, comprising:

a. a first housing having at least one interior wall and an exterior wall, said at least one interior wall defining a substantially cylindrical chamber, said chamber having a first end, a second end, a chamber axis and at least one diameter, at least one of said first end and second end having an end wall having a bearing opening;

b. a valve shaft positioned within said chamber, said valve shaft having n end hub and a valve shaft axis of rotation aligned with said chamber axis, said valve shaft capable of rotation about said valve shaft axis of rotation;

c. valve shaft bearings held in said bearing opening and receiving said shaft for rotation;

d. rotor coupled to said shaft for rotation therewith positioned at one of said first end and second end opposite said end wall, said rotor having a rotor bearing surface having one or more channels;

e. stator having at least one stator exterior surface and at least one stator interior surface, said stator interior surface having a stator bearing surface said stator bearing surface for receiving a rotor bearing surface and allowing said rotor bearing surface to rotate in relation to said stator bearing surface, said stator removably received about said end of said chamber opposite said bearing opening, said stator having at least two stator fluid openings, each of said stator fluid openings extending from said stator exterior to said rotor bearing surface in alignment with said one or more channels to define an open position upon the rotor assuming a first position and in alignment with a rotor bearing surface without one or more channels upon the rotor assuming a second position to define a closed position, said first position defining an open position in which fluids are received in one of said stator fluid openings and flow through said channel and out a second stator fluid opening and a closed position in which fluids are prevented from flowing from one stator fluid opening to the other stator fluid opening by means of the rotor bearing surface;

f. pressure means for pressing said rotor bearing surface against said stator bearing surface such that rotation of the valve shaft and rotor allows fluid flow in one valve shaft position and does not allow fluid flow in a second valve shaft position said pressure means engaging said end wall and said valve shaft;

g. at least one key opening having a position in one of the group selected from the rotor and the end hub, said key opening in cooperation with and receiving a key pin associated with the rotor and end hub that does not have the key opening, such that said rotor rotates with said rotor shaft, wherein said key pin has a stop abutment surface and said housing has a stop element projecting from the cylindrical wall for preventing angular rotation of the rotor with respect to the housing.

36. A device for controlling the flow of fluid in a conduit, comprising:

a. a first housing having at least one interior wall and an exterior wall, said at least one interior wall defining a substantially cylindrical chamber, said chamber having a first end, a second end, a chamber axis and at least one diameter, at least one of said first end and second end having an end wall having a bearing opening;

b. a valve shaft positioned within said chamber, said valve shaft having a valve shaft axis of rotation aligned with said chamber axis, said valve shaft capable of rotation about said valve shaft axis of rotation, and said shaft has toothed coupling for receiving cooperating toothed coupling on a power shaft;

c. valve shaft bearings held in said bearing opening and receiving said shaft for rotation;

d. rotor coupled to said shaft for rotation therewith positioned at one of said first end and second end opposite said end wall, said rotor having a rotor bearing surface having one or more channels;

e. stator having at least one stator exterior surface and at least one stator interior surface, said stator interior surface having a stator bearing surface said stator bearing surface for receiving a rotor bearing surface and allowing said rotor bearing surface to rotate in relation to said stator bearing surface, said stator removably received about said end of said chamber opposite said bearing opening, said stator having at least two stator fluid openings, each of said stator fluid openings extending from said stator exterior to said rotor bearing surface in alignment with said one or more channels to define an open position upon the rotor assuming a first position and in alignment with a rotor bearing surface without one or more channels upon the rotor assuming a second position to define a closed position, said first position defining an open position in which fluids are received in one of said stator fluid openings and flow through said channel and out a second stator fluid opening and a closed position in which fluids are prevented from flowing from one stator fluid opening to the other stator fluid opening by means of the rotor bearing surface; and, f. pressure means for pressing said rotor bearing surface against said stator bearing surface such that rotation of the valve shaft and rotor allows fluid flow in one valve shaft position and does not allow fluid flow in a second valve shaft position said pressure means engaging said end wall and said valve shaft, g. a second housing having a first section and a second section, said first section holding said first housing and said second section comprising at least one interior wall, one exterior wall and one end wall, said interior wall defines a cylindrical chamber, and said end wall terminating said chamber, said end wall having a opening for receiving a power shaft, said chamber for containing a transmission for receiving power from a motor comprising one or more gears constructed and arranged to transfer rotational force from a motor to said power shaft.

37. The device of claim 36 further comprising a motor coupled to said transmission to rotate said power shaft.

38. The device of claim 36 wherein said second housing contains power shaft sensing means, said power shaft sensing means producing one or more signals in response to the rotational position of said power shaft.

39. The device of claim 36 further comprising a centering ring for aligning and retaining said first housing to said second housing.

* * * * *